US012622720B2

(12) United States Patent
Dorfmüller et al.

(10) Patent No.: US 12,622,720 B2
(45) Date of Patent: May 12, 2026

(54) DEVICE FOR GENERATING SHOCKWAVES

(71) Applicant: Heart Regeneration Technologies GmbH, Innsbruck (AT)

(72) Inventors: Christian Dorfmüller, Rielasingen (DE); Johannes Holfeld, Innsbruck (AT)

(73) Assignee: Heart Regeneration Technologies GmbH, Innsbruck (AT)

( * ) Notice: Subject to any disclaimer, the term of this patent is extended or adjusted under 35 U.S.C. 154(b) by 0 days.

(21) Appl. No.: 18/814,111

(22) Filed: Aug. 23, 2024

(65) Prior Publication Data

US 2025/0072921 A1 Mar. 6, 2025

(30) Foreign Application Priority Data

Sep. 4, 2023 (EP) .................................... 23195028

(51) Int. Cl.
*A61B 17/225* (2006.01)
*A61B 17/00* (2006.01)

(52) U.S. Cl.
CPC .. *A61B 17/225* (2013.01); *A61B 2017/00199* (2013.01); *A61B 2017/00477* (2013.01); *A61B 2017/00836* (2013.01); *A61B 2017/00862* (2013.01)

(58) Field of Classification Search
None
See application file for complete search history.

(56) References Cited

U.S. PATENT DOCUMENTS

| | | | |
|---|---|---|---|
| 4,608,983 A | 9/1986 | Mueller et al. | |
| 4,702,249 A | 10/1987 | de la Fonteijne | |
| 4,844,198 A | 7/1989 | Ferralli | |
| 5,329,928 A | 7/1994 | Brisson et al. | |
| 5,793,001 A | 8/1998 | Ferralli | |
| 5,903,386 A | 5/1999 | Mantravadi et al. | |

(Continued)

FOREIGN PATENT DOCUMENTS

| | | |
|---|---|---|
| CN | 103594081 | 2/2014 |
| DE | 2538960 | 4/1977 |

(Continued)

OTHER PUBLICATIONS

Mittal et al., "Soft Computing Research," IEEE, eNewsletter, 2009 Issue #29, 2009.

(Continued)

*Primary Examiner* — Yi-Shan Yang
(74) *Attorney, Agent, or Firm* — Lewis & Reese, PLLC

(57) ABSTRACT

The invention relates to a device for generating shockwaves. The device comprises a pressure pulse source comprising a chamber housing defining a chamber (22) and a shockwave opening (21). The chamber (22) is configured to be filled with a liquid. The device comprises a plurality of electrodes disposed in the chamber (22) and configured to be coupled to a pulse-generation system, the plurality of electrodes including a first electrode and a second electrode, the first electrode and the second electrode defining a spark gap. The chamber (22) additionally includes a maintenance opening (16), wherein the maintenance opening (16) is sealed by a port (30) for manipulating the chamber (22) through the port (30).

16 Claims, 6 Drawing Sheets

(56) References Cited

U.S. PATENT DOCUMENTS

| | | | |
|---|---|---|---|
| 6,036,661 A | 3/2000 | Schwarze et al. | |
| 11,096,706 B2 | 8/2021 | Dorfmuller et al. | |
| 2004/0092865 A1* | 5/2004 | Flaherty | A61M 5/1452 604/93.01 |
| 2005/0038361 A1 | 2/2005 | Zhong | |
| 2007/0016112 A1* | 1/2007 | Schultheiss | A61B 90/30 601/4 |
| 2008/0146971 A1 | 6/2008 | Uebelacker et al. | |
| 2008/0262434 A1* | 10/2008 | Vaillancourt | A61M 5/158 604/192 |
| 2011/0034832 A1 | 2/2011 | Cioanta et al. | |
| 2014/0257144 A1 | 9/2014 | Capelli et al. | |
| 2022/0168500 A1* | 6/2022 | Mccaffrey | A61M 5/16881 |

FOREIGN PATENT DOCUMENTS

| | | |
|---|---|---|
| DE | 19718511 | 11/1998 |
| DE | 10065450 | 7/2002 |
| WO | 2011/006017 | 1/2011 |
| WO | 2023/015047 | 2/2023 |

OTHER PUBLICATIONS

Zhou et al., "The Effect of Reflector Geometry on the Acoustic Field and Bubble Dynamics Produced by an Electrohydraulic Shock Wave Lithotripter," J. Acoustic Sock Am. 2006, 119(6), 3625-3636, 2006.

Yang et al., "Deastigmatism and Circulatization of an Elliptical Gaussian Bearn by Off-Axis Ellipsoid Reflector Based Off-Focus Configuration," Progress in Electromagnetics Research B, vol. 10, 91-103, 2008.

Extended European Search Report regarding corresponding European Application No. 23195028.8, mailed Feb. 12, 2024.

* cited by examiner

200

210

220

100

1

112

110

111

115

50

40

30

20

18

1

DEVICE FOR GENERATING SHOCKWAVES

CROSS REFERENCE TO RELATED APPLICATIONS

This application claims priority to European Application Serial No. 23195028.8, filed Sep. 4, 2023, which is incorporated herein by reference in its entirety.

FIELD OF THE INVENTION

The present invention relates to a device for generating shockwaves. Further, the present invention relates to a set comprising the device and to a method of manipulating the device.

INTRODUCTION

For several decades shockwaves at low-energy levels have been known, mainly in orthopedics and wound healing. The first human medical application of high-energy extracorporeal shockwaves was in the field of urology using its mechanical characteristics in liquids to destroy urinary concernments within the patient's body. For example, such shockwaves are used to destroy kidney stones. This medical procedure is known as lithotripsy. A further application of shockwaves is Direct Epicardial Shock Wave Application, DESWT. DESWT induces tissue regeneration in infarcted heart muscle and thereby significantly improves and restores heart function (left ventricular ejection fraction). The shockwaves initiate biological responses like new heart muscle tissue formation.

Shockwaves in the above applications may be generated electro-hydraulically. Electro-hydraulic shockwave generation means that a liquid is held in a closed chamber with at least two electrodes inside. A high voltage is applied between the two electrodes, for example a multiple of 1 kV (including 1 kV). Upon an electrical discharge between the two electrodes a part of the liquid is vaporized by a plasma generated by the electrical discharge between the electrodes. This causes an acoustic shock wave pressure pulse in the liquid (typically water) which is then transferred via a membrane to the patient's skin or tissue. Some shockwave generators additionally include a reflector for focusing the shockwaves energy to a certain point or a geometrical form like a ring or a line, depending on the designated treatment area within the patient's body. For example, an ellipsoidal reflector may focus the point like shockwave generated between the tips of the electrodes in the first focal point of into a second focal point. The second focal point which is typically positioned within the patient's body and defined as the treatment area. Alternatively, a parabolic reflector may generate flat unfocused parallel shockwave pressure fronts like in the treatment of skin burns and other superficial occurring treatment indications. If there is no reflector, the shockwaves radiate spherically from the electrical discharge between the electrode tips. These unfocused shock waves are used in the treatment of arteriosclerosis within coronary arteries by electrodes inserted via a coronary catheter.

Many of the above medical indications can be treated by using a small handheld shock wave applicator (shock wave probe). The electrodes in the probe are eroded by the energies generated during the electrical discharge for the shockwave generation. Therefore, the electrodes must be exchanged or refurbished after a certain number of generated shockwaves. The amount of erosion of the electrodes increases with the applied electrical energy and therefore depends on the selected acoustic energy level of the shockwaves. This causes a limit to the maximum number of shock wave released by a single shockwave probe. The probe has by this limitation a predefined capacity of shock wave releases before the distance between the electrode tips is enlarged by the erosion to an amount that the electrical discharge will no longer ignite properly with a resulting imperfect shockwave generation.

To achieve a reliable functioning of the electro-hydraulic therapeutic shockwaves system the probes are exchangeable to a basic control and power unit. This concept allows to have several probes in stock at the medical site with a defined number of shockwaves to be generated for therapeutic purposes as described above. If one probe has reached its maximum number (capacity) of shock wave releases, it can be unplugged from the basic power and control unit and exchanged by the user. This allows to use probes with different specific and adapted shock wave characteristics by different focusing reflectors, different liquids compositions for physical different pathways of shock wave generation, different penetration depths by different filling levels of the probe's liquid.

The used probes can be technically refurbished by exchanging the eroded electrodes and by exchanging the liquid level for different penetration depths and by changing the liquid composition. It might also be necessary for certain probes to refurbish, because theirs shelf lifetime has been reached by losing liquid by diffusion through the flexible coupling membrane. The liquid will be refilled, and the composition adjusted in an alternative refurbishment procedure.

For different application schemes there might be different probes as a part of a product family. These different types of probes need all be to be stored at the medical treatment site to have all the desired different focusing characteristics on site. The number of probes to be stored is increasing rapidly when different penetration depths, different focusing characteristics and different composition of the liquid are required. The liquid within the probe can influence the penetration depth by increasing the membrane protrusion or influencing the physics of the electrical discharge between the tips of the electrodes and thereby the effectiveness of the shockwave generation. The liquid compositions added within the probe can be acids, salt solutions, conductive, semiconductive or isolation particle suspensions.

Shockwave probes as described above are typically manufactured by a supplier and then shipped to a medical professional or hospital. However, shockwaves generated by known shockwave probes change over time. For example, a part of the liquid within the chamber may evaporate leading to a deterioration of the device. Thus, over time, the filling of the closed chamber with liquid will diminish. It is suspected that a part of the liquid diffuses through the membrane by water vapor diffusion. Further, the electrical properties of the liquid may change over time altering shockwave generation. In addition, there is limited flexibility in changing the properties of the generator's shockwaves of the known devices.

An object of the present invention is to provide a device for generating shockwaves, which overcomes one or more of the above-mentioned problems of the prior art. In particular, it is an object of the present invention to provide a device for generating shockwaves with a long shelf life, that can be flexibly adjusted on-site, for example by a technician or user on-site.

SUMMARY

A first aspect of the invention provides a device (also "probe" herein) for generating shockwaves, comprising a pressure pulse source comprising a chamber housing defining a chamber and a shockwave opening. The chamber is configured to be filled with a liquid. The device further comprises a plurality of electrodes disposed in the chamber and configured to be coupled to a pulse-generation system. The plurality of electrodes include a first electrode and a second electrode. The first electrode and the second electrode define a spark gap. The chamber additionally includes a maintenance opening, wherein the maintenance opening is preferably sealed by a port or valve for manipulating the chamber through the port or valve.

A pressure pulse or shockwave may be an acoustic pulse which includes several cycles of positive and negative pressure. The amplitude of the positive part of such a cycle may be above 0.1 MPa to 100 MPa. In preferred embodiments, the range is between 10 and 100 MPa. A time duration of a pressure pulse or shockwave may be below a microsecond to about a second. In preferred embodiments the duration is from 0.5 μs to 10 μs.

The chamber housing defines a chamber. Additionally, the pressure pulse source may comprise a membrane. The membrane may cover the shockwave opening. Together, the membrane and the chamber housing may define a closed chamber for shockwave generation. The closed chamber is configured to be filled with a liquid. In some embodiments, the closed chamber comprises the liquid, and is preferably filled with the liquid. In a preferred embodiment the liquid is water. The term liquid may include any liquid substances including mixtures, solutions, suspensions, and dispersions. The liquid may additionally comprise additive substances or materials. The additive substances or materials may, e.g., change the conductivity of the liquid. The conductivity and filling (e.g., pressure) of the liquid influences the underwater spark discharge characteristics and therefore the lag times and rise times and intensity of the electro-hydraulic shockwaves that are generated within the chamber. Exemplary additives are salts, for example sodium chloride (NaCl), graphite particles, and metallic and semiconductive particles. Such additives allow for improving the characteristics of the electrical spark or plasma formation when applying a high voltage to the tips of the electrodes.

The device comprises a plurality of electrodes, i.e., at least two electrodes. The electrodes maybe spaced apart by a spark gap such that a spark can form between them when a high voltage as described above is applied. In some embodiments the electrodes may be adjustable to influence the lag time for the spark formation or compensate the distance for the erosion of the electrode tips. The electrodes may be adjustable by mechanical means which can be automated and motorized.

According to claim 1, the chamber includes a shockwave opening and an additional maintenance opening. The maintenance opening is preferably sealed by a port for manipulating the chamber through the port. The port prevents the liquid within the chamber from leaving the chamber. According to the invention, the maintenance opening allows adding and removing liquid from the chamber. In case liquid has evaporated from the chamber and the pressure pulses generated by the device do not satisfy the requirements, a user may add or remove liquid from the chamber. Previously, a shelf life of a device as described above was limited by the diffusion of liquid from the chamber (for example through the membrane sealing the shockwave opening). The maintenance opening allows a user to adjust the fill level of the chamber without needing to return the device to the manufacturer. The port may be held by the chamber housing, in particular it may be directly held in the chamber housing.

The port may be screwed into or otherwise mechanically attached to the chamber housing (e.g., snap fit, rivetted, press-fit, glued, integrally formed with the chamber housing, etc.). A direct attachment, as e.g., opposed to a port in a connected tube or hose, may provide the advantage of a lower liquid volume and avoiding propagation of pressure waves through the additional liquid volume. Holding the port directly in the chamber housing has the advantage, that a particularly simple construction is enabled. Tools for adding or removing liquid or additives may be provided separately from the device.

The maintenance opening connects the chamber with the outside. The maintenance opening may be closer to the membrane than electrode openings. Additionally, or alternatively, the maintenance opening may be radially outside as compared to the electrode openings or at the same radial position. Thereby, the maintenance opening interferes less with the reflection of the generated shockwaves.

Preferably, the maintenance opening does not point towards the spark gap of the electrodes or the center of the chamber housing. The maintenance opening may define a maintenance opening channel that does not point towards the spark gap or the center of the chamber housing. The maintenance opening may define a maintenance opening channel that extends parallel to the one or two electrodes or electrode openings. The maintenance opening channel may extend at an angle of 10°, 20°, 30°, 40° 45° or more to a radial direction, i.e., the direction towards the spark gap of the electrodes or the center of the housing. Thereby, an interference with the shockwaves is reduced.

In addition, a user may add or remove liquid to modify the properties of the pressure within chamber. An increase in pressure will extend the membrane curvature and increase the quality of the acoustic coupling with the skin or tissue. In case of fixed focus reflectors the penetration depth of the focus distance to the aperture may be increased or reduced by adding or removing liquid. Adding liquid may increase the pressure in the chamber and thereby increase the pressure on the membrane and serves for a higher pressure when coupling the membrane to the patient's skin or tissue. Removing liquid may reduce the pressure in the chamber and thereby reduce the pressure of on the membrane and the pressure for coupling.

Further, a user may modify the properties of the liquid within the chamber. For example, particles modifying the conductivity of the liquid may be added. Salts, graphite particles, metallic particles, and/or semiconductive particles or even non-conductive particles may be added to modify lag times, rise times and/or the intensity of the electro-hydraulic shockwaves that are generated.

Preferably, the port is self-scaling. A self-sealing port may allow for a particularly easy interaction. The user can change the composition and the content of the chamber as described above without needing to close the port after the modification.

Preferably, the port comprises an elastic material. Thereby, a particularly tight sealing can be ensured. The elastic material ensures that a good seal is formed that prevents liquid from escaping the chamber. In one particular embodiment, the port may be or comprise an elastic plug or an inflatable bladder that is held directly in the maintenance opening channel.

Preferably, the port defines a port channel and wherein the elastic material seals the port channel. Thereby, the elastic material may be removed and replaced if needed without difficulty.

Preferably, the elastic material extends over the entire cross-section of the port channel. The port may include a bushing that is at least partially filled with elastic material. The elastic material may form an elastic plug or an inflatable bladder that is held in the port channel. This provides for a particularly simple implementation of a port. Further, the plug can be removed and/or replaced, if needed. In a further embodiment, the elastic material extends over a part or an entire length of the port channel.

Preferably, the elastic material is disk-shaped or cylindrically shaped. Such ports may be pierced with a needle or syringe and a user may add or remove liquid or additives using a punching or non-punching needle. Since devices as described above are typically used in a medical environment (e.g., a doctor's office or hospital) the tools needed for modifying the device for generating shockwaves are already available. A user does not need to acquire specialized tools for modifying the contents of the closed chamber.

Preferably, the elastic material is compressed. Thereby, a part of the port is pre-stressed, and the port is sealed as a default setting. In a further implementation of the device according to the first aspect, the elastic material is or comprises silicone (Si), PP (Polypropylene), PE-LD (Polyethylene Low density), PE-LLD (Polyethylene linear Low density), PE-HD (Polyethylene high density), PE-MD (Polyethylene high density), PVC (Polyvinylchloride), PUR (Polyurethane), PET (Polyethylene terephthalate) and other thermoplastics and elastomers. These materials exhibit elastic properties and can seal the maintenance opening channel or port channel.

Preferably, the port comprises a bushing for releasably connecting the port to the housing. For example, the port may include a threading. This provides for a particularly simple construction and a replaceable port. In another embodiment the port can be press-fit or glued into the housing.

Preferably, the device further comprises a reflector for redirecting and shaping a shockwave pattern generated by the pressure pulse source; and a membrane or lens covering said reflector for transmitting said shockwave pattern. The reflector may be ellipsoidal, parabolic or of other geometrical conic sections.

A second aspect of the invention provides a set comprising a device according to one of the previous claims, and a needle for penetrating the port. In a further implementation of the device of the second aspect, the needle is a Huber needle or Gripper needle.

A third aspect of the present invention relates to a method of manipulating a device for generating shockwaves. In the method, first a device as described above is provided. Then, the content of the chamber is manipulated through the port. In a preferred embodiment of the method, the manipulation comprises adding a liquid or a solid to the chamber and/or removing liquid from the chamber. In some embodiments, the port defines a port channel and an elastic material seals the port channel. The method comprises the step of providing a needle, in particular a Huber or Gripper needle and penetrating the elastic material with the needle. Then, the content of the chamber can be manipulated through the needle, e.g., by adding or removing liquid with a syringe. Then, the needle is removed from the port. As the elastic material may be pre-stressed, the chamber is automatically closed again thereafter.

BRIEF DESCRIPTION OF THE DRAWINGS

The invention will be described by way of example and with reference to the accompanying drawings.

6

Figure 1B:
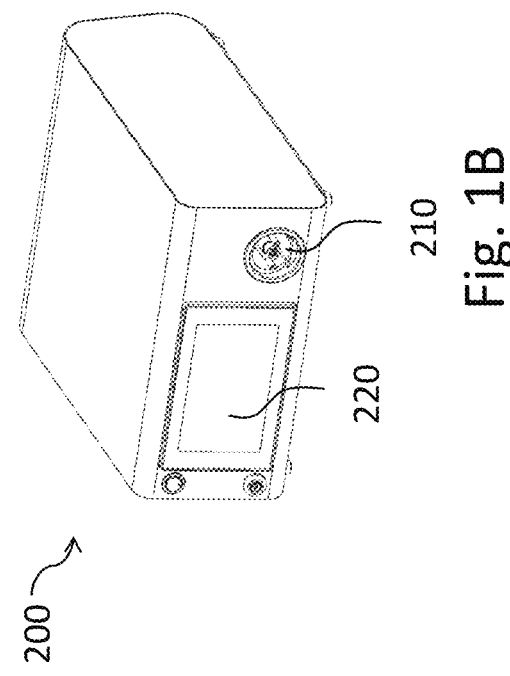
Figure 1A:
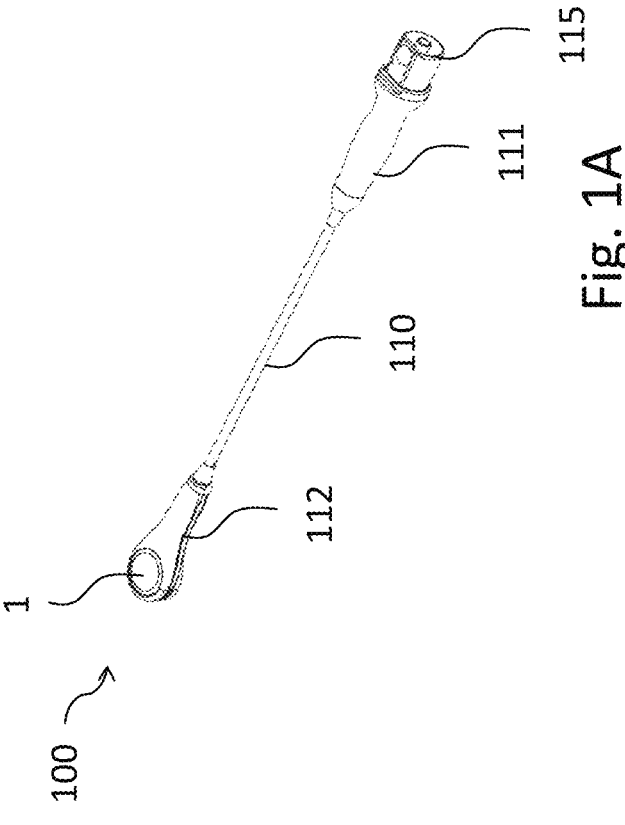

FIG. 1A is a perspective view of a shockwave applicator comprising a device according to the invention.

FIG. 1B is a power and control unit for the shockwave applicator of FIG. 1A.

Figure 2B:
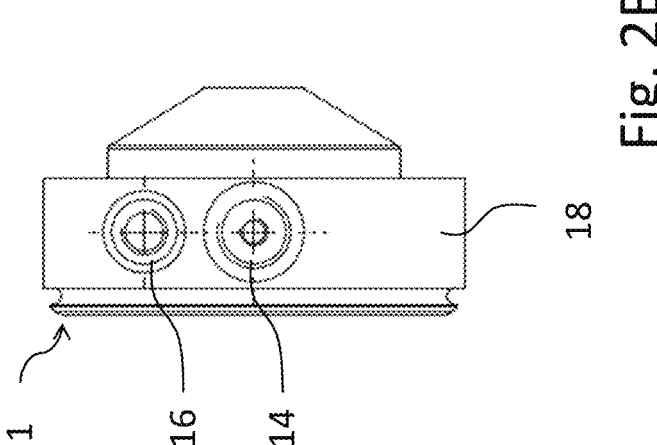
Figure 2A:
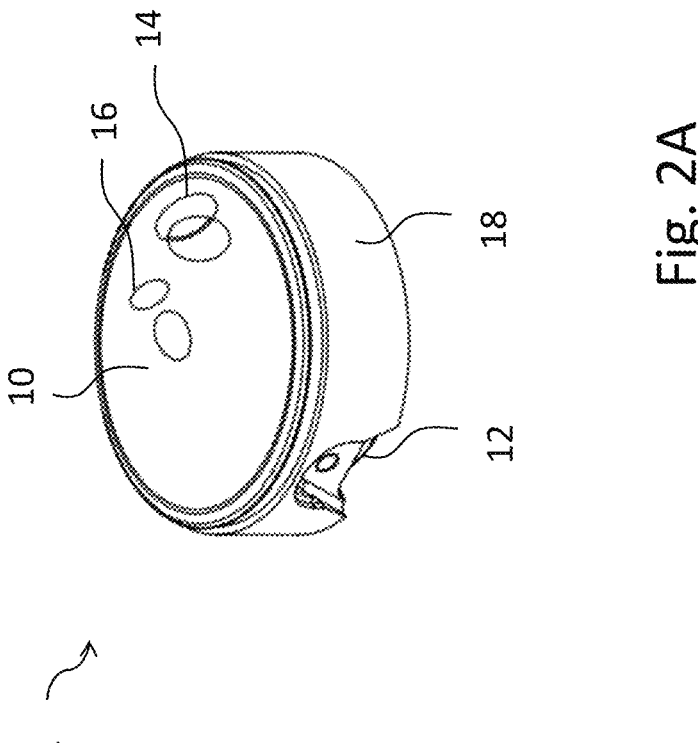

FIG. 2A shows a perspective view of the device (reflector and chamber when sealed with the membrane) for generating shockwaves according to FIG. 1A.

FIG. 2B is a side view of the device (reflector and chamber when sealed with the membrane) for generating shockwaves according to FIG. 2A.

Figure 3:
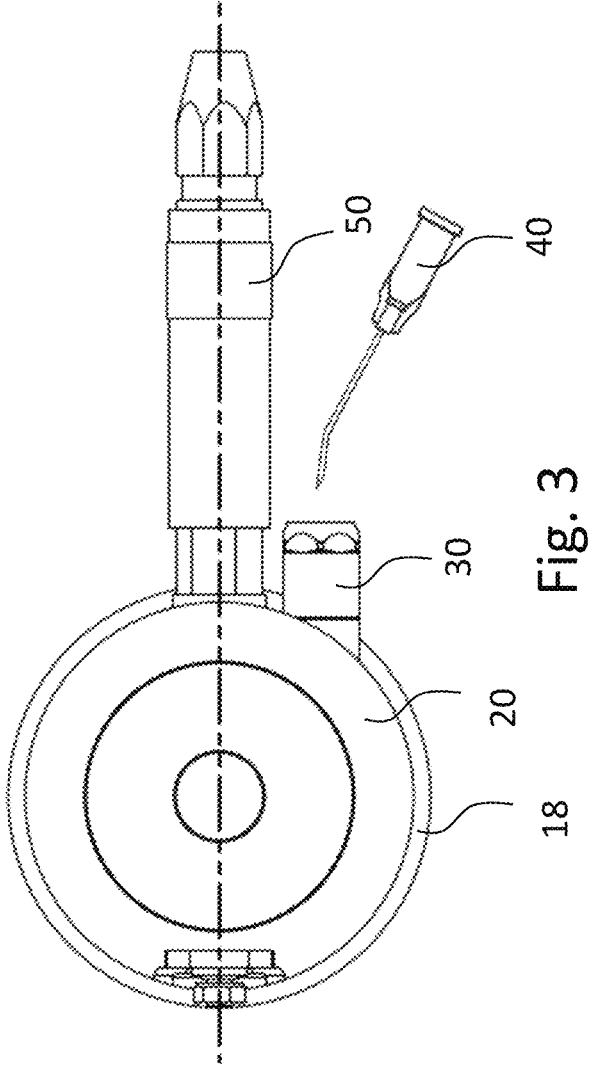
Figure 3:

FIG. 3 is a bottom view of the shockwave applicator without a part of a housing.

Figure 4B:
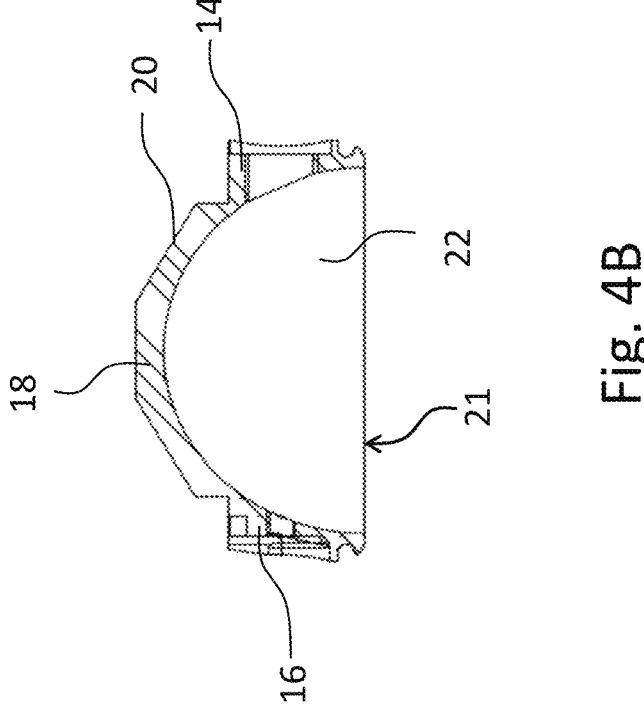
Figure 4A:
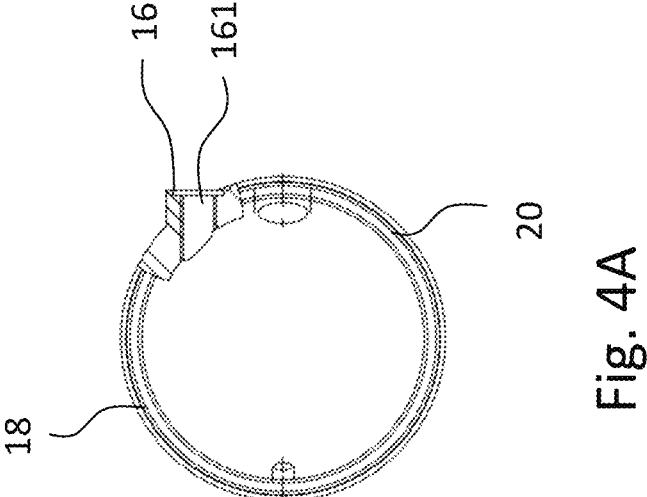

FIG. 4A is a top view of the device for generating shockwaves according to FIG. 2A.

FIG. 4B is a cross-section of the device (through the central horizontal line) for generating shockwaves according to FIG. 2A.

Figure 5:
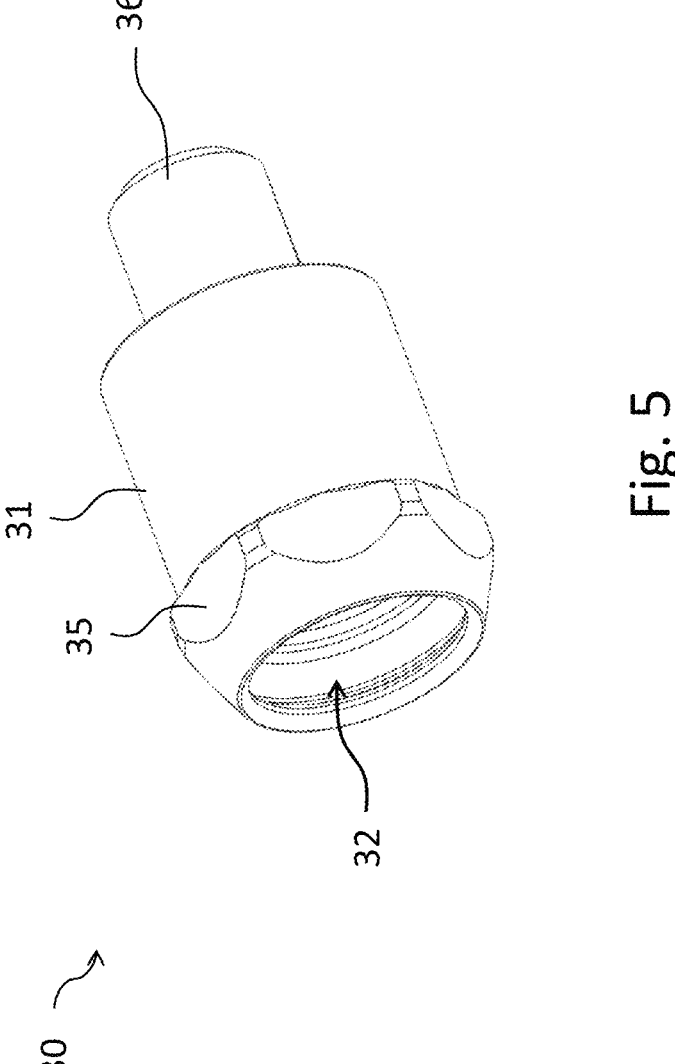

FIG. 5 shows a port for a maintenance opening in a perspective view.

Figures 6A, 6B:
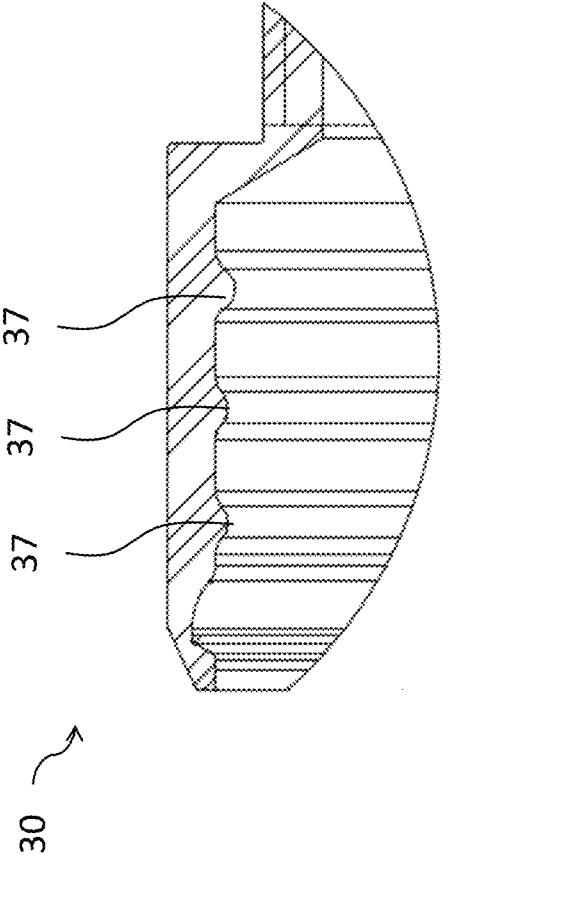

FIG. 6A shows a side view of the port of FIG. 5.

FIG. 6B shows a part of a cross-section of the port of FIGS. 5 and 6A.

DETAILED DESCRIPTION

With reference to FIGS. 1A and 1B, a portable hand-held shockwave applicator device 100 and a power and control unit 200 are illustrated (i.e., an acoustic pulse-generation system). The hand-held shockwave applicator device 100 includes a cable 110. One end of the cable 110 comprises a connector 111 and the other end of the cable 110 comprises a housing 112. Within the housing 112, a shockwave generating device 1 (also device for generating shockwaves herein) is arranged. The connector 111 can be connected to a corresponding female receptacle 210 of the power and control unit 200. The power and control unit 200 may also include a touchscreen 220 for operation of the power and control unit 200. The connector 111 includes a male end portion 115 that can be inserted into the female receptacle 210. The cable 110 may be a high voltage cable or rod and is preferably surrounded by an elastomeric insulation.

FIGS. 2A, 2B, 3, 4A and 4B show the shockwave generating device 1 in further detail. The shockwave generating device 1 includes a channel 10 for a membrane (see FIG. 2A). The membrane transmits shockwaves generated within device 1 into a body of a patient. The shockwave generating device 1 is held within the housing 112 (FIG. 1A) and connected to the cable 110 at a cable connection. FIGS. 2A and 2B show the shockwave generating device 1 without the housing 112 and without the electrodes. FIG. 2B shows a side view of the device 1 shown in FIG. 2A. The shockwave generation device 1 comprises a chamber housing 18. The chamber housing 18 includes electrode openings 12 and 14. The electrode openings 12 and 14 receive electrodes and center and hold the electrodes for spark generation. The electrode openings 12 and 14 are arranged at opposing sides of the housing and arranged along a line through a center of the chamber housing 18. A chamber 22 is formed within the chamber housing 18 (see e.g., FIG. 4B) and sealed by the membrane. The chamber 22 is formed by, e.g., a parabolic reflector 20 and the membrane and filled with liquid during operation, i.e., shockwave generation. The tips of the electrodes are gapped at a distance to facilitate a spark gap which creates the shockwave when energized. In the side view of FIG. 2B, it is apparent that in addition to cable connection port 14, the device 1 comprises a maintenance port 16.

FIG. 3 shows further details of the device 1 in a top view from the bottom of the ellipsoidal reflector 20, i.e., an outside shape of the chamber housing 18. In the view of FIG. 3, the housing 112 is removed. The ellipsoidal reflector 20 opens to the bottom forming a shockwave opening 21 (see FIG. 4B). The ellipsoidal reflector 20 and the membrane may thus form a chamber housing. FIG. 3 further shows a connecting portion 50 of the shockwave generating device 1 to the cable 110. The connecting portion 50 may include elastomeric insulation bellows, a magnet and a coil for moving the magnet. This may be used to adjust a distance between electrodes. Alternatively, the tips can be replaced with adjustable electrodes using other means such as piezo ceramics, magnets, motors with gear boxes, pneumatics or hydraulics to change the tip distance. In addition, FIG. 3 shows a portion of port 30. As can be seen, a Huber needle 40 can be inserted into the port 30 to add or remove liquids or solids from the chamber.

FIG. 4A shows a cross-section through a portion of the device 1. The cross-section is close to the membrane and shows a maintenance port or opening 16 for the port 30. In the view shown in FIGS. 4A and 4B the port 30 is not depicted. The maintenance opening 16 is formed as a maintenance opening channel 161 which may comprise an inner threading, pass fit or being glued. Further, the channel may include a flange or protrude from the reflector 20 as shown in FIG. 4A. The maintenance opening channel 161 may be directed towards the center, or as shown in FIG. 4A, extend in a direction parallel to one of the electrode openings 12 and 14 and is optionally spaced apart from a symmetry axis of the reflector 20. The maintenance opening 16 may be closer to the membrane than the electrode openings and may be radially outside or at the same radial position as compared to the electrode openings (see FIGS. 2A and 2B).

FIG. 4B shows a second cross-section of the device 1 and in particular of the reflector 20. As can be seen, the reflector 20 in this example is ellipsoidal. The reflector may be metallic. The reflector may partially surround tips of the electrodes. The reflector 20 opens to the membrane (see FIG. 2A) and the internal surface provides the shape of the emitted wave patterns as a function of its geometric shape. The reflector 20 can be made of a numerous variety of shapes to achieve a desired wave pattern as known in the art. In the shown examples, the reflector 20 is formed by the chamber housing 18.

FIGS. 5, 6A and 6B show the port 30 in detail. The port 30 comprises an outer housing 31. The outer housing 31 may be a bushing or hollow sleeve or hollow sheath. The outer housing 31 forms a port channel 32 in which an elastic port material is held (not shown). The elastic port material is disc-shaped and has a larger diameter than the port channel 32 of the outer housing 31. The elastic port material is pushed into the port channel 32 with force and thus under radial pressure. The elastic material may have a larger width or diameter than the port channel 32. Due to the pressure, the elastic material (for example silicone) forms a tight seal with the outer housing 31. Further, the elastic material may be penetrated by a Huber needle 40 as shown in FIG. 3 and then reseal the port channel 32 of the port 30 after removal of the Huber needle 40. A first end of the outer housing 31 of the port 30 includes chamfered faces 35 such that the port 30 can be inserted into the maintenance opening 16 with a wrench. In addition, an end portion 36 of the port 30 includes an outer threading fitting into the inner threading of the maintenance opening 16. Thus, the port 30 can be screwed, press fit or glued into the maintenance opening 16 as is known in the art. FIG. 6B shows a detail of a cross-section of the port 30. The port channel 32 includes ribs 37. The ribs 37 hold the elastic material in the port channel 32 in place, in particular when a needle is inserted and removed through the elastomeric material held within the port channel. The ribs 37 extend circumferentially. In alternatives the ribs may also extend longitudinally or helically or have any other desirable shape or direction.

What is claimed is:

1. A device for generating shockwaves, comprising:
a pressure pulse source comprising a chamber housing defining a chamber and a shockwave opening, the chamber being configured to be filled with a liquid; and
a plurality of electrodes disposed in the chamber and configured to be coupled to an electrical pulse-generation system, the plurality of electrodes including a first electrode and a second electrode, the first electrode and the second electrode defining a spark gap,
wherein the chamber additionally includes a maintenance opening, wherein the maintenance opening is sealed by a port for manipulating the chamber through the port.

2. The device according to claim 1, wherein the port is self-sealing.

3. The device according to claim 1, wherein the port comprises an elastic material.

4. The device according to claim 3, wherein the port defines a port channel and wherein the elastic material seals the port channel.

5. The device according to claim 4, wherein the elastic material extends over the entire cross-section of the port channel.

6. The device according to claim 3, wherein the elastic material is disk-shaped or cylindrically shaped.

7. The device according to claim 3, wherein the elastic material is radially compressed.

8. The device according to claim 3, wherein the elastic material is silicone.

9. The device according to claim 1, wherein the port comprises a bushing for releasably connecting the port to the housing.

10. The device according to claim 1, further comprising:
a reflector for redirecting and shaping a shockwave pattern generated by the pressure pulse source; and
a membrane or lens covering the reflector for transmitting the shockwave pattern.

11. A system, comprising:
the device for generating the shockwaves according to claim 1; and
a needle for penetrating the port.

12. The system according to claim 11, wherein the needle is a Huber needle or Gripper needle.

13. A method of manipulating a device for generating shockwaves, comprising:
providing the device for generating the shockwaves according to claim 1; and
manipulating a content of the chamber through the port.

14. The method according to claim 13, wherein manipulating comprises adding a liquid or solid to the chamber and/or removing liquid from the chamber.

15. The method according to claim 13, wherein the port defines a port channel and wherein an elastic material seals the port channel, the method further comprising:
providing a needle;
penetrating the elastic material with the needle;
manipulating a content of the chamber through the needle; and
removing the needle from the port.

16. The method according to claim 15, wherein the needle comprises a Huber or Gripper needle.

\* \* \* \* \*